United States Patent [19]

Preston

[11] 4,010,755
[45] Mar. 8, 1977

[54] UNIPOLAR PACING CATHETER WITH PLURAL DISTAL ELECTRODES

[76] Inventor: Thomas A. Preston, 820 37th Ave., Seattle, Wash. 98122

[22] Filed: May 27, 1975

[21] Appl. No.: 580,876

Related U.S. Application Data

[63] Continuation-in-part of Ser. No. 309,996, Nov. 28, 1972, Pat. No. 3,893,461.

[52] U.S. Cl. .......................... 128/404; 128/419 P
[51] Int. Cl.² .......................................... A61N 1/04
[58] Field of Search ............... 128/404, 418, 419 P, 128/421, 422

[56] References Cited

UNITED STATES PATENTS

| | | | |
|---|---|---|---|
| 3,478,746 | 11/1969 | Greatbatch | 128/419 P |
| 3,638,656 | 2/1972 | Grandjean et al. | 128/419 P |
| 3,788,329 | 1/1974 | Friedman | 128/418 |
| 3,815,611 | 6/1974 | Denniston | 128/419 P |
| 3,825,015 | 7/1974 | Berkovits | 128/404 |

*Primary Examiner*—William E. Kamm
*Attorney, Agent, or Firm*—Woodcock Washburn Kurtz & Mackiewicz

[57] ABSTRACT

A flexible catheter apparatus is adapted to be positioned in a patient for use in cardiac pacing, with a first electrode positioned within the heart, and a second one positioned outside the heart. In the preferred embodiment, the first electrode includes a plurality of spaced apart conducting bands located within about 2 cm of the end of the catheter. The bands are electrically connected and are two or more in number, with one such band located at about the distal end of the catheter, and at least another located about 1.0 cm from the distal end.

8 Claims, 4 Drawing Figures

U.S. Patent    Mar. 8, 1977    4,010,755
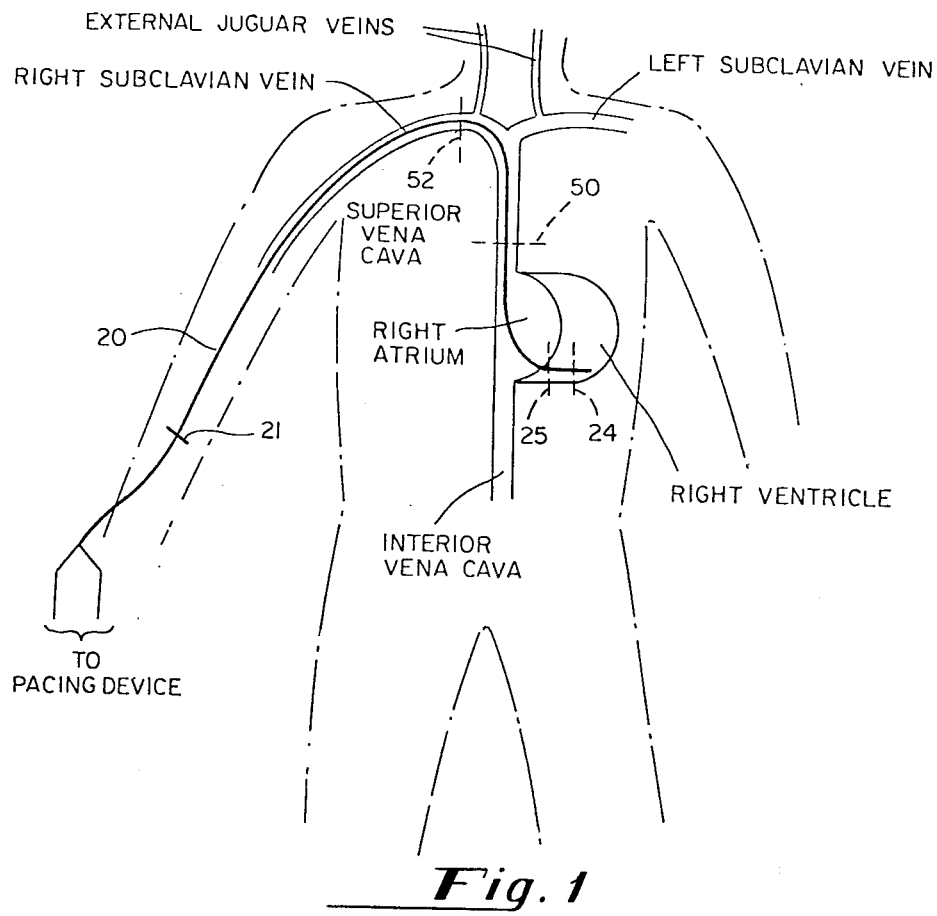
*Fig. 1*
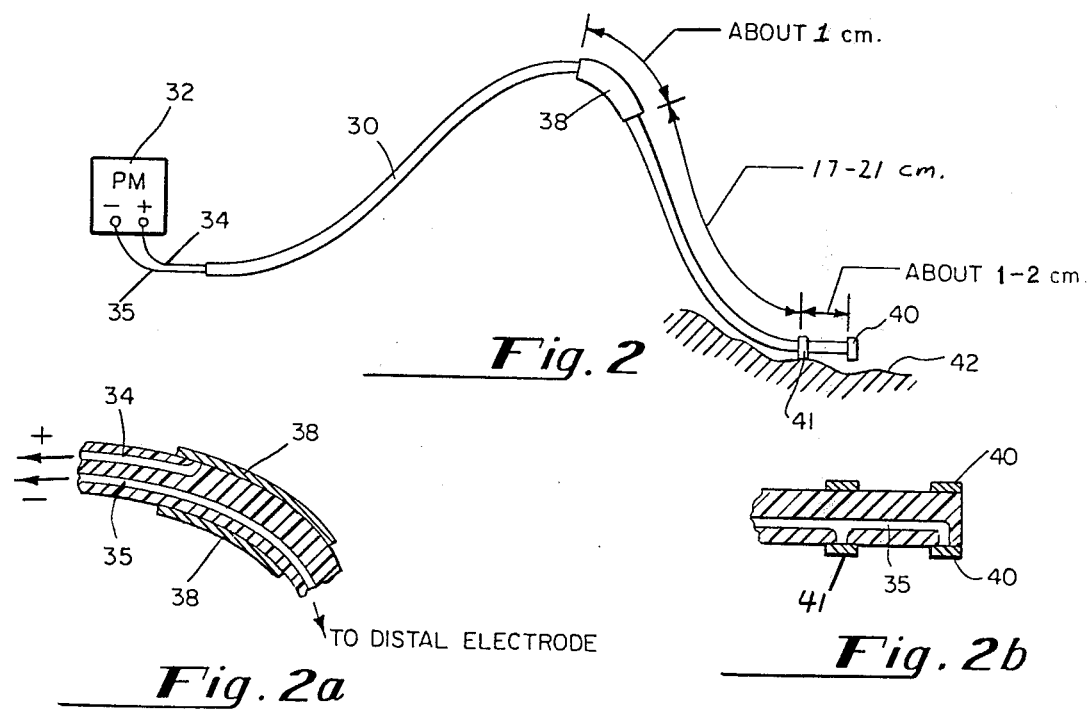
*Fig. 2*
*Fig. 2a*
*Fig. 2b*

UNIPOLAR PACING CATHETER WITH PLURAL DISTAL ELECTRODES

CROSS-REFERENCE TO RELATED APPLICATIONS

The application is a continuation-in-part of my co-pending application Ser. No. 309,996, filed Nov. 28, 1972 issued on July 8, 1975 as U.S. Pat. No. 3,893,461.

BACKGROUND OF THE INVENTION

This invention relates to heart pacing apparatus. More particularly, it relates to catheters used with external and implanted pacers for temporary and permanent pacing in a clinical environment.

Temporary pacing of a patient in the post-operative period following cardiac surgery is an established and effective means of treating arrhythmias or increasing cardiac output. Additionally, temporary pacing is particularly important and widely used with respect to complete heart block, especially in patients undergoing acute myocardial infarction. Such temporary pacing has been a widely used clinical procedure in this country for many years, and the technique of inserting the catheter into the patient and pacing from an external source is a common technique of cardiology. A number of instrument manufacturers produce clinically acceptable catheters, and there are several models of pacing apparatus well known to cardiologists and suitable for carrying out this technique.

There have been two basic types of catheters available and in use for such external, or temporary pacing. A first type is what is referred to as a unipolar catheter, having one lead extending substantially the length of the catheter and being electrically connected to an electrode which is positioned inside the patient's heart for transmitting the desired electrical signal thereto. This cardiac electrode is connected through the catheter lead to a first terminal of a pacing device which, in temporary pacing, is external to the patient, and which is designed to produce a desired periodic pacing signal. The second terminal of the external pacer is connected to an electrode which is generally clamped to the patient's skin around or near the point of entry of the catheter, which may be approximately at the large vein opposite the patient's right elbow. Another suitable site, such as in the femoral vein, may also be used for catheter insertion. Such electrode must be maintained in firm electrical contact with the patient, usually requiring some sort of electrically conductive paste be applied to the patient's skin, as well as the use of additional means (such as suturing an electrode beneath the skin at the site of incision) for maintaining the electrode in firm position. When the electrodes are connected to the Pacemaker, the periodic output signals from the pacing device terminals produce biopotentials in the patient's heart of a character so as to induce stimulation of the heart, i.e., so as to pace the heart.

The second type of standard catheter in common use, is what is referred to as a bipolar catheter, having both electrodes positioned near the distal end of the catheter, such that when the catheter is fully inserted into the patient's heart, both electrodes are inside the heart and in proper position to transmit the desired signal from the pacing device directly to the patient's heart. Using the bipolar catheter, the two leads of the catheter are simply connected directly to the external pacing device, or to whatever device is in clinical use.

In a co-pending application, Ser. No. 309,996, filed Nov. 28, 1972 and which issued on July 8, 1975 as U.S. Pat. No. 3,893,461, I have disclosed a novel catheter arrangement wherein a first electrode is located substantially at the distal end of the catheter, and a second electrode is located sufficiently proximal to the distal electrode that it lies outside the heart when the catheter is positioned for pacing. The distal electrode is positioned within the heart, such that contact thereof with the heart wall provides a conduction path for the pacing signals. As set forth in that co-pending application, it is advantageous that the distal electrode be negative in polarity, i.e., operate as the cathode, relative to the proximal electrode which operates as the anode, so as to achieve cathodal pacing. Hereinafter, that application shall be referred to as "my referenced co-pending application", and is incorporated herein by reference.

In any cardiac pacing system, the stimulus signal must exceed the patient's threshold in order that a response be evoked. The threshold in turn is a function of the positioning of the catheter within the heart. In permanent implant systems, care is taken to position the catheter optimally, but in temporary pacing the catheter frequently is not placed with such care. In a small percentage of temporary pacing cases, highly variable thresholds have been encountered, occasionally resulting in transient failure to pace. While this phenomenon seems to be rare with bipolar pacing, more frequent occurrences have been reported in the literature from the early unipolar pacing art.

It accordingly is a primary object of the present invention to provide unipolar pacing apparatus having an optimal design with respect to pacing threshold variability.

It is a further object to provide such apparatus while preserving the advantageous operation of unipolar pacing relative to arrhythmias, fibrillation, or similar pathologies common to bipolar pacing.

SUMMARY OF THE INVENTION

The present invention is based on my conclusion that occasional pacing threshold irregularities for unipolar apparatus are based on poor placement of the distal electrode within the heart, with the variable separation between the electrode and the endocardium accounting for the threshold change. This conclusion is based on the hypothesis that bipolar pacing avoids the irregular threshold problems since with both electrodes located within the heart, the probability is that one or the other will be in substantial contact with the endocardium, and therefore that pacing will occur from one of the electrodes even if the other is floating. This conclusion in turn is based on clinical measurments and evaluations.

In accordance with the foregoing, the present invention involves methods and apparatus for providing unipolar cathodal pacing which substantially avoids threshold irregularities. In particular, adequate contact between the distal electrode and the endocardium is assured by providing spaced, multiple distal electrode bands electrically connected to one another, at least one of which is in position to contact the irregular endocardial surface when the catheter is in the right ventricle. Clinical results indicate that two separated bands, located within about 1–2 cm of the distal end of the catheter, achieve the desired results.

In an illustrative embodiment, a flexible catheter is equipped with two electrical leads therein, a first one being connected to a proximal electrode band positioned on the catheter so as to be situated outside the heart when the catheter is fully inserted such that its distal tip is lodged in the right ventricle. The second lead is coupled to first and second distal electrode bands, one being positioned at the distal end of the catheter and the other being positioned between 1.0 and 2 cm from the first. In a preferred mode of operation, signals coupled to the distal electrode are negative in polarity relative to the potential of the proximal electrode.

BRIEF DESCRIPTION OF THE DRAWINGS

FIG. 1 is a diagrammatic sketch showing placement of a catheter within the human body, which schematically illustrates electrode placement in accordance with the principles of the present invention.

FIG. 2 shows a catheter with preferred electrode placement in accordance with the principles of the present invention, and FIGS. 2a and 2b show cross-sectional views of the FIG. 2 catheter in the areas of the electrodes.

DESCRIPTION OF THE PREFERRED EMBODIMENT

FIG. 1 symbolically illustrates a temporary pacing catheter positioned for operation. From the figure, the pacing device is seen to be located outside the body, and the catheter 20 is inserted at the point of entry 21 in the arm, commonly into the right basilic vein. The catheter is advanced from that point through the right subclavian vein, the superior vena cava, the right atrium, and into the right ventricle. In accordance with prior art schemes and with the principles of the present invention, the end of the catheter is preferably somewhat wedged into the ventricle such that contact is made between the distal end of the catheter and the endocardium.

Still referring to FIG. 1, the points 24 and 25, which are within the right ventricle, correspond roughly to the location of the cathode and anode of conventional bipolar catheter apparatus. For the unipolar methods and apparatus set forth in my referenced co-pending application, the cathode is located approximately at point 24 on the catheter 20, and the anode is situated outside the heart, approximately between points 50 and 52 of the catheter. In accordance with the principles of the present invention, a unipolar catheter is presented having an anode located so as to be positioned outside the heart, approximately between points 50 and 52 of the catheter 20, and a multiple band cathode is located so as to be positioned in the range between point 24 and the end of the catheter. That is, electrode 38 is positioned typically 18-23 cm from the distal tip of the catheter, and distal electrode 40-41 is positioned near the distal tip. In practicing the method of this invention, the catheter is inserted so that electrode 38 is positioned outside the heart and electrode 40-41 is positioned within the right ventricle.

FIGS. 2, 2a, and 2b show various views of catheter apparatus embodying the principles of the present invention. From the figures, the catheter is seen to be an elongated, flexible instrument 30 having a pair of electrically conductive leads 34 and 35 encased in a substantially inert, non-conductive casing such as Teflon, nylon, or other similar materials well known in the art. The leads 34 and 35 are coupled to a pacing device 32.

Electrically, the catheter of FIG. 2 is designed to work in the unipolar cathodal mode as set forth in my referenced co-pending application. Accordingly, located approximately 18-23 cm from the distal end of the catheter is an electrode 38 which is electrically connected to the positive lead 34 as set forth in FIG. 2a, so that it functions as the anode when so connected. Advantageously, the anode electrode 38 is formed of a cylindrical surface about 1 cm long, and is located outside the patient's heart when the catheter is in place for pacing.

At the distal end of the catheter is an electrode suitable for pacing, which in accordance with the principles of the present invention constitutes multiple conducting bands 40 and 41. As shown in FIG. 2b, the lead 35 is coupled through the catheter material 30 to the bands 40 and 41 which are tied together electrically.

The separation of the bands advantageously is in the 1 cm – 2 cm range to contact the irregular muscle ridges of the endocardium. In a preferred embodiment, the bands 40 and 41 are situated within 2 cm of the distal end of the catheter. However, it is noted that this spacing may be as great as 6 cm, or as small as 0.5 cm. The preferred location for the end band 40 is at the distal terminus of the catheter 30. As in the case of the apparatus disclosed in my referenced co-pending application, it is desirable that the proximal electrode 38 be larger in surface area than the distal electrode. In a preferred embodiment, the respective bands 40 and 41 of the distal electrode are approximately 2 to 3 mm in width.

The advantageous functioning of catheters involving the principles of the present invention is shown in FIG. 2, in which there is schematically illustrated the irregular surface of the endocardium. Even when the catheter 30 is well wedged into the ventricle, a mere single pacing electrode may still be spaced away from the actual surface of the endocardium due to the surface irregularities. My studies have shown that a single electrode must be within 2-4 mm of the endocardial surface to pace the heart with electrical impulses commonly applied. Provision for multiple electrode bands, i.e., 2 or more, in accordance with the principles of the present invention, however, insures that almost always contact is made by one or another band of the distal electrode. Accordingly, the threshold variation difficulties attendant to single electrode band unipolar catheters are obviated and a stable threshold is maintained.

It is to be noted that, while a continuous larger single band distal electrode might also insure contact with the endocardial ridges, the electric field concentration produced thereby would be excessive. Thus, the multiple, smaller bands allow for the same assurance of contact but maintain the field strength at allowable levels.

It is to be noted that the catheter of applicant's invention simultaneously serves three important functions. First, it enables positioning of one electrode in the heart and one electrode out of the heart, for the desired form of unipolar cathodal pacing. Second, it enables positioning of both the electrodes safely distant from the atrium, for sensing in a demand pacer mode of operation. Note that if the distal electrode, or any band thereof, is positioned too far proximal from the distal tip of the catheter, there is incurred a great likelihood that it will be positioned in the atrium, which condition would be unacceptable for sensing in connection with demand pacing. Using applicant's catheter, with the distal and proximal electrodes separated preferably at least 17 cm, the two electrodes can be safely used for both pacing, and sensing of natural beats. And third, the catheter provides for a more stable threshold due to the relative independence of exact positioning in the ventricle, as provided by the multiple bands.

I claim:

1. Catheter apparatus adapted to be positioned in a patient for use in cardiac pacing of the patient, with a predetermined distal end extending into the patient's heart, comprising:
   a. an elongated flexible catheter tube having two conducting leads extending through respective lengths thereof;
   b. a proximal electrode of predetermined surface size connected electrically to a first one of said leads;
   c. a distal electrode, positioned at about said distal end, having at least two conducting bands surrounding said catheter tube and of respective predetermined surface areas, said bands being positioned within 2 cm of said distal end, each of said conducting bands electrically connected to the second one of said leads, said conducting bands being separated, such that said distal electrode comprises a plurality of electrically connected bands having only non-conducting surfaces therebetween; and
   d. said proximal electrode being positioned on said catheter at least 17 cm proximal to said distal electrode.

2. The apparatus as described in claim 1, further including pacing means, for generating electrical pacing signals, having first and second terminals respectively connected to said two leads at the end of said catheter opposite said predetermined distal end, said pacing signals being presented across said terminals.

3. Apparatus as described in claim 2, wherein said pacer is connected so that said proximal electrode is an anode, and said distal electrode is a cathode.

4. The apparatus as described in claim 3, wherein said distal electrode has two bands separated by a distance of between 1.0 and 2.0 cm.

5. The catheter apparatus as described in claim 1, wherein a first of said conducting bands is at said distal end and the other is positioned within 1 to 2 cm from said end.

6. The catheter apparatus as described in claim 5, wherein said bands are 2 to 3 mm in width.

7. The catheter apparatus as described in claim 6, wherein said proximal electrode comprises a band having a cylindrical surface about 1 cm long.

8. Catheter apparatus adapted to be positioned in a patient for use in cardiac pacing of the patient, said apparatus having a predetermined distal end for positioning into the patient's heart, comprising:
   a. an elongated flexible catheter tube having two conducting leads extending through respective lengths thereof;
   b. a proximal electrode having a cylindrical surface and connected electrically to the first one of said leads;
   c. a distal electrode, positioned at said distal end, having a plurality of conducting bands surrounding said catheter tube and having widths of about 2–3 mm, one of said bands being located at said distal tip, said bands being positioned within 6 cm of said distal end, each of said conducting bands being electrically connected to the second one of said leads and being separated, such that said distal electrode comprises said plurality of conducting bands connected in common electrically and having only non-conducting surfaces therebetween; and
   d. said proximal electrode being positioned on said catheter at a distance at least 17 cm proximal to the most proximal of said distal electrode bands.

* * * * *